(12) United States Patent
Kosnik et al.

(10) Patent No.: US 7,422,900 B1
(45) Date of Patent: Sep. 9, 2008

(54) SYSTEM AND METHOD FOR FORMING A CONNECTIVE TISSUE CONSTRUCT

(75) Inventors: Paul E. Kosnik, Bay City, MI (US); Robert G. Dennis, Ann Arbor, MI (US); Sarah C. Calve, Darien, CT (US); Ellen M. Arruda, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 734 days.

(21) Appl. No.: 10/602,789

(22) Filed: Jun. 24, 2003

Related U.S. Application Data

(60) Continuation-in-part of application No. 09/709,890, filed on Nov. 9, 2000, now Pat. No. 6,777,234, which is a division of application No. 09/153,721, filed on Sep. 15, 1998, now Pat. No. 6,207,451.

(51) Int. Cl.
*C12N 5/00* (2006.01)
(52) U.S. Cl. .................. 435/395; 435/325; 435/283.1; 435/305.1; 435/402; 435/177; 435/182; 623/13.11; 623/13.17; 623/13.14
(58) Field of Classification Search ................ 435/395, 435/325, 283.1, 305.1, 402, 177, 182; 623/1.47, 623/13.11, 13.14, 13.17
See application file for complete search history.

(56) References Cited

U.S. PATENT DOCUMENTS

| | | | |
|---|---|---|---|
| 4,605,623 A | 8/1986 | Malette et al. | |
| 4,642,292 A | 2/1987 | Reid et al. | |
| 4,801,299 A | 1/1989 | Brendel et al. | |
| 4,940,853 A | 7/1990 | Vandenburgh | |
| 5,153,136 A | 10/1992 | Vandenburgh | |
| 5,443,950 A | 8/1995 | Naughton et al. | |
| 5,618,718 A | 4/1997 | Auger et al. | |
| 5,756,350 A * | 5/1998 | Lee et al. | 435/325 |
| 6,114,164 A | 9/2000 | Dennis et al. | |
| 6,207,451 B1 | 3/2001 | Dennis et al. | |
| 6,303,286 B1 | 10/2001 | Dennis et al. | |
| 6,448,076 B2 | 9/2002 | Dennis et al. | |

OTHER PUBLICATIONS

Nordin, M. et al., Biomechanics of Tendons and Ligaments, In: Nordin, M. nd Frankel V.H., eds. Basic Biomechanics of the Musculoskeletal System, New York: Lippincott Williams & Wilkins, 2001, pp. 102-125.
Cao, Y.L. et al., Bridging Tendon Defects Using Autologous Tenocyte Engineered Tendon in a Hen Model, Plastic and Reconstructive Surgery, 110, 1280, 2002.
Bell, E. et al., Production of a Tissue-Like Structure by Contraction of Collagen Lattices by Human-Fibroblasts of Different Proliferative Potential In Vitro, Proceedings of the National Academy of Sciences of the United States of America, 76, 1274, 1979.
Brown, R.A. et al., Tensional Homeostatis in Dermal Fibroblasts: Mechanical Responses to Mechanical Loading in Three-Dimensional Substrates, Journal of Cellular Physiology, 175, 323, 1998.
Cacou, C. et al., A System for Monitoring the Response of Uniaxial Strain on Cell Seeded Collagen Gels, Medical Engineering & Physics, 22, 327, 2000.
Dennis, R.G. and Kosnik, P.E. Mesenchymal Cell Culture: Instrumentation and Methods for Evaluating Engineered Muscle. In: Atala, A. and Lanza R.P., eds. Methods of Tissue Engineering. New York: Academic Press, 2002, pp. 307-315.
Fung, Y.C., Biomechanics: Mechanical Properties of Living Tissues. New York: Springer, 1993, pp. 252-263.
Parry, D.A.D.and Craig, A.S., Growth and Development of Collagen Fibrils in Connective Tissue. In: Ruggeri, A. and Motta, P.M. eds. Ultrastructure of the Connective Tissue Matrix. Boston: M. Nijhoff Publishers, 1984, pp. 34-64.
Vandenburgh et al., Skeletal Muscle Growth is Stimulated by Intermittent Stretch-Relaxation in Tissue Culture, American Psych, Society, 1989, pp. C674-C682.
Vandenburgh, A Computerized Mechanical Cell Stimulator for Tissue Culture Effects on Skeletal Muscle Organogensis, In Vitro Cellular & Development Biology, vol. 24, No. 7, Jul. 1988, pp. 609-619.
Vandenburgh et al. Longitudinal Growth of Skeletal Myotubes In Vitro in a New Horizontal Mechanical Cell Stimulator, In Vitro Cell Dev. Bio., vol. 25, No. 7, Jul. 1989, pp. 607-616.
Vandenburgh et al., Computer-Aided Mechanogenesis of Skeletal Muscle Organs from Single Cells In Vitro, The FASEB Journal, vol. 5, Oct. 1991, pp. 2860-2867.
Vandenburgh et al., Tissue-Engineered Skeletal Muscle Organoids for Reversible Gene Therapy, Human Gene Therapy, Nov. 1996, pp. 2195-2200.
Butler, D.L. and Awad, H.A., Perspectives on Cell and Collagen Composites for Tendon Repair, Clinical Orthopaedics and Related Research, 367, S324-S332, 1999.
Goldstein, J.D. et al., Development of a Reconstituted Collagen Tendon Prosthesis—A Preliminary Implantation Study, Journal of Bone and Joint Surgery-American vol. 71A, 1183-1191, 1989.
Iannace, S., Mechanical-Behavior of Composite Artificial Tendons and Ligaments, Biomaterials, 16, 675-680, 1995.
Shansky et al., Letter to the Editor: A Simplified Method for Tissue Engineering Skeletal Muscle Organoids In Vitro, In Vitro Cell. Dev. Biol., Oct. 1997, pp. 659-661.
McBride, D.J. et al., Morphological Characterization of Tendon Development During Chick Embryogenesis—Measurement of Birefringence Retardation, International Journal of Biological Macromolecules, 7, 71-76, 1985.

(Continued)

*Primary Examiner*—L. Blaine Lankford
(74) *Attorney, Agent, or Firm*—Brooks Kushman P.C.

(57) ABSTRACT

A system and method are provided for forming a connective tissue construct, such as a tendon construct, in vitro. A substrate is provided with at least two anchors secured thereto in spaced relationship. Fibroblast cells are provided on the substrate in the absence of a synthetic matrix, where at least some of the cells are in contact with the anchors. The cells are cultured in vitro under conditions to allow the cells to self-organize and become confluent between the anchors, where the anchors are receptive to the cells and allow the cells to attach thereto while permitting the cells to detach from the substrate to form a three-dimensional connective tissue construct.

37 Claims, 3 Drawing Sheets

OTHER PUBLICATIONS

Torres, D.S. et al., Tendon Cell Contraction of Colagen-GAG Matrices In Vitro: Effect of Cross-Linking, Biomaterials, 21, 1607-1619, 2000.

Koob, T.J. and Hernandez, D.J., Material Properties of Polymerized NDGA-Collagen Composite Fibers: Development of Biologically Based Tendon Constructs, Biomaterials, 23, 203-212, 2002.

Huang, D. et al., Mechanisms and Dynamics of Mechanical Strengthening in Ligament-Equivalent Fibroblast-Populated Collagen Matrices, Annals of Biomedical Engineering, 21, 289-305, 1993.

Wakatsuki, T. et al., Cell Mechanics Studied by a Reconstituted Model Tissue, Biophysical Journal, 79, 2353-2368, 2000.

Seliktar, D. et al., Dynamic Mechanical conditioning of Collagen-Gel Blood Vessel Constructs Induces Remodeling In vitro, Annals of Biomedical Engineering, 28, 351-362, 2000.

Holmes, D.F. et al., Reconstitution of Collagen Fibrils In Vitro—The Assembly Process Depends on the Initiating Procedure, International Journal of Biological Macromolecules, 8, 161-166, 1986.

Birk, D.E. and Zycband, E., Assembly of the Tendon Extracellular Matrix During Development, Journal of Anatomy, 184, 457-463, 1994.

Nurminskaya, M.V. and Birk, D.E. Differential Expression of Genes Associated with Collagen Fibril Growth in the Chicken Tendon: Identification of Structural and Regulatory Genes by Subtractive Hybridization, Archives of Biochemistry and Biophysics, 350, 1-9, 1998.

Murrell, G.A.C. et al., Effects of Immobilization on Achilles-Tendon Healing in a Rat Model, Journal of Orthopaedic Research, 12, 582-591, 1994.

Gelberman, R.H. et al., The Early States of Flexor Tendon Healing—A Morphologic Study of the First 14 Days, Journal of Hand Surgery-American vol., 10A, 776-784, 1985.

Dennis, R.G. and Kosnik, P.E., Excitability and Isometric Contractile Properties of Mammalian Skeletal Muscle Constructs Engineered In Vitro, In Vitro Cellular Development Biology-Animal, 36, 327-335, 2000.

Kurata, S. and Hata, R., Epidermal Growth-Factor Inhibits Transcription of Type-I Collagen Genes and Production of Type-I Collagen in Cultured Human Skin Fibroblasts in the Presence and Absence of L-Ascorbic Acid 2-Phosphate, A Long-Acting Vitamin-C Derivatie, Journal of Biological Chemistry, 266, 9997-10003, 1991.

Betsch, D.F. and Baer, E., Structure and Mechanical Properties of Rat Tail Tendon, Biorheology, 17, 83-94, 1980.

McBride, D.J. et al., Structural and Mechanical Assessment of Developing Chick Tendon, International Journal of Biological Macromolecules, 10, 194-2000, 1988.

Haut, T.L. and Haut, R.C., The State of Tissue Hydration Determines the Strain-Rate-Sensitive Stiffness of Human Patellar Tendon, Journal of Biomechanics, 30, 79-81, 1997.

Kang, H.J. and Kang, E.S., Ideal Concentration of Growth Factors in Rabbit's Flexor tendon Culture, Yonsei Medical Journal, 40, 26-29, 1999.

Ishikawa, O. et al., Morphological and Biochemical Analyses on Fibroblasts and Self-Produced Collagens in a Novel Three-Dimensional Culture, British Journal of Dermatology, 136, 6-11, 1997.

Hall, B.K. and Herring, S.W., Paralysis and Growth of the Musculoskeletal in the Embryonic Chick, Journal of Morphology, 206, 45-56, 1990.

Germiller, J.A. et al., Muscle and Tendon Size Relationships in a Paralyzed Chick Embryo Model of Clubfoot, Journal of Pediatric Orthopaedics, 18, 314-318, 1998.

Beckham, C. et al., Role of Movement in Development of a Digital Flexor Tendon, American Journal of Anatomy, 150, 443-460, 1977.

Postacchini, F. and DeMartino, C., Regeneration of Rabbit Calcaneal Tendon Maturation of Collagen and Elastic Fibers Following Partial Tenotomy, Connective Tissue Research, 8, 41-47, 1980.

Wantanabe, M. et al., Maturation-Related Biochemical-Changes in Swine Anterior Cruciate Ligament and Tibialis Posterior Tendon, Journal of Orthopaedic Research, 12, 672-682, 1994.

Amiel, D. et al., Tendons and Ligaments: A Morphological and Biochemical Comparison, Journal of Orthopaedic Research, 1, 257-265, 1984.

* cited by examiner

SYSTEM AND METHOD FOR FORMING A CONNECTIVE TISSUE CONSTRUCT

CROSS-REFERENCE TO RELATED APPLICATIONS

This application is a continuation-in-part of U.S. application Ser. No. 09/709,890 filed Nov. 9, 2000 now U.S. Pat. No. 6,777,234, which is a divisional of U.S. application Ser. No. 09/153,721 filed Sep. 15, 1998, now U.S. Pat. No. 6,207,451.

STATEMENT REGARDING FEDERALLY SPONSORED RESEARCH OR DEVELOPMENT

The invention was made with Government support under Contract No. N66001-02-C-8034 from DARPA (Contracting Agent: SPAWAR) and under Contract No. CMS 9988693 from the National Science Foundation (CMS Division).

BACKGROUND OF THE INVENTION

1. Field of the Invention

This invention relates to the field of tissue engineering, and more particularly to a system and method for producing a connective tissue construct, such as a tendon construct, in vitro.

2. Background Art

There are approximately 33 million musculoskeletal injuries each year in the United States. The associated soft tissues, which include tendons, comprise almost 50% of these injuries. In some cases, the tendon is damaged beyond repair, and partial or whole replacement of the tendon is necessary. The ideal replacement would be autologous tendon, but transplantation is limited by the availability of viable autograft tissue. As a result, clinical practice has turned to the use of synthetic materials (see Goldstein et al., *Journal of Bone and Joint Surgery—American Volume,* 71A, p. 1183, 1989), where current synthetic replacements include DACRON® grafts, carbon fibers, and silastic sheets. Unfortunately, these materials are unable to adequately restore function for the long term due to their inherent mechanical incompatibility with the in vivo environment as well as their tendency to degrade (see Iannace et al., *Biomaterials,* 16, p. 675, 1995).

Tendons are densely packed connective tissues that transmit the forces between muscle and bone. They are stiff in tension, yet flexible enough to conform to their anatomical environment. The material properties of tendon tissue can be attributed to the parallel fibrils of collagen which make up approximately 75% of the dry weight of adult tendons. In the resting state, the fibrils display a periodic wavy pattern, defined as the crimp. As a tendon is stretched, the crimped collagen fibrils begin to straighten out and may cause the tendon to become stiffer with increasing mechanical strain. Tendons have a low cell density, around 20% of the tissue volume, but fibroblasts are integral in the development and maintenance of the tissue. The distinct spatial orientation of tendon fibroblasts is associated with the organization of collagen fibers into the hierarchical tendon structure.

Because of its relatively avascular nature, tendon is a prime candidate for engineered tissue replacement. Previous attempts have been made to create biologically based tendons in vitro, but these have met with limited success due to the difficulty in creating an in vitro tissue, or "construct", that is both mechanically and biologically compatible with the in vivo environment (see Butler and Awad, *Clinical Orthopedics and Related Research,* 367, p. S324, 1999; Goldstein et al., *Journal of Bone and Joint Surgery—American Volume,* 71A, p. 1183, 1989; Torres et al., *Biomaterials,* 21, p. 1607, 2000; Cao et al., *Plastic and Reconstructive Surgery,* 110, p. 1280, 2002; Koob and Hernandez, *Biomaterials,* 23; p. 203, 2002).

Mechanical difficulties can arise from the reliance on artificial scaffolds when attempting to engineer tendon. Type I collagen is the most widely used scaffold material since it was observed that fibroblasts will contract a collagen gel to form a tissue-like structure (see Bell et al., *Proceedings of the National Academy of Sciences of the United States of America,* 76, p. 1274, 1979). Collagen would appear to be the ideal foundation for an artificial tendon, but presently the mechanical properties of in vitro fibroblast-collagen constructs are inferior to those of native tissues (see Huang et al., *Annals of Biomedical Engineering,* 21, p. 289, 1993; Wakatsuki et al., *Biophysical Journal,* 79, p. 2353, 2000; Seliktar et al., *Annals of Biomedical Engineering,* 28, p. 351, 2000; Brown et al., *Journal of Cellular Physiology,* 175, p. 323, 1998; Cacou et al., *Medical Engineering & Physics,* 22, p. 327, 2000).

An explanation for this discrepancy is that gelled collagen is generally disorganized and only forms fibrils of physiological thickness under stringent conditions (see Holmes et al., *Journal of Biological Macromolecules,* 8, p. 161, 1986). Furthermore, native tendons possess an extracellular matrix (ECM) composed of many proteins, glycosaminoglycans, and proteoglycans which control the assembly of the collagen fibril, the load bearing unit, and contribute to the formation of the tissue hierarchy. Fibroblasts rely on cell-matrix signaling pathways during development to properly assemble the fibrils and maintain form and function after maturation. Koob and Hernandez created a mechanically relevant construct by cross-linking extruded collagen fibers with NGDA, a plant derived anti-oxidant, for which only ultimate strengths were reported and not the entire elastic response (see Koob and Hernandez, *Biomaterials,* 23; p. 203, 2002). Goldstein et al. used the same idea of creating a fiber composite to create artificial prostheses, but relied upon cross-linking methods that were cytotoxic and/or non-biodegradable (see Goldstein et al., *Journal of Bone and Joint Surgery—American Volume,* 71A, p. 1183, 1989).

Accordingly, a need exists for a tendon construct that incorporates as many of the native properties of tendon as possible in order to sufficiently restore function.

SUMMARY OF THE INVENTION

It is an object according to the present invention to provide a system and method for producing a connective tissue construct in vitro.

It is another object according to the present invention to provide a system and method for inducing tendon fibroblasts to self-assemble into a three-dimensional tendon construct.

It is another object according to the present invention to provide a system and method for producing a tendon construct that self-organizes without the need for exogenous scaffolding.

Accordingly, a system for forming a connective tissue construct is provided which includes a substrate and at least two anchors secured to the substrate in spaced relationship. Fibroblast cells are provided on the substrate in the absence of a synthetic matrix, where at least some of the cells are in contact with the anchors. The cells are cultured in vitro under conditions to allow the cells to become confluent between the anchors, where the anchors are receptive to the cells and allow the cells to attach thereto while permitting the cells to detach from the substrate to form a three-dimensional connective tissue construct.

According to the present invention, the fibroblast cells can be derived from tendon tissue, or alternatively could be derived from ligament tissue or other connective tissue. The fibroblast cells can also be derived from stem cells. In another embodiment, myogenic precursor cells can be cultured in combination with the fibroblast cells. The fibroblast cells self-organize to form the three-dimensional tissue construct.

The anchors preferably include silk suture segments coated with cell adhesion molecules, where the cell adhesion molecules can include laminin. The anchors can also include a bone-like substrate. The substrate is coated with cell adhesion molecules, such as laminin. In a preferred embodiment, the concentration of laminin is about 1.5 to 3.0 $\mu g/cm^2$. In addition, the cell adhesion molecules can include thrombin. Preferably, the substrate and anchors are incubated with a growth medium prior to providing fibroblast cells on the substrate.

According to the present invention, the fibroblast cells are preferably disposed in a growth medium prior to becoming confluent, and are disposed in a differentiation medium after becoming confluent. The fibroblast cells are also preferably supplemented with ascorbic acid, most preferably approximately 100 $\mu g/ml$ of L-ascorbic acid 2-phosphate.

In further accordance with the present invention, a system for forming a tendon construct is provided. The system includes a substrate and at least two anchors secured to the substrate in spaced relationship. The system further includes a medium including fibroblast cells and ascorbic acid provided on the substrate, where at least some of the cells are in contact with the anchors. The cells are cultured in vitro under conditions to allow the cells to self-organize and become confluent between the anchors, and the anchors are receptive to the cells and allow the cells to attach thereto while permitting the cells to detach from the substrate to form a three-dimensional tendon construct.

Correspondingly, a method for forming a connective tissue construct is provided. The method includes providing a substrate and securing at least two anchors to the substrate in spaced relationship. The method further includes providing fibroblast cells on the substrate in the absence of a synthetic matrix, where at least some of the cells are in contact with the anchors. Still further, the method includes culturing the fibroblast cells in vitro under conditions to allow the cells to become confluent between the anchors, where the anchors are receptive to the cells and allow the cells to attach thereto while permitting the cells to detach from the substrate and form a three-dimensional connective tissue construct.

According to the method of the present invention, providing fibroblast cells includes deriving the fibroblast cells from tendon tissue, or alternatively from ligament tissue, other connective tissue, or stem cells. The fibroblast cells can be harvested from mammalian tissue, and the resulting construct can be implanted in a suitable donor. The fibroblast cells can also be cultured in combination with myogenic precursor cells. Culturing the fibroblast cells allows for self-organization of the into the three-dimensional connective tissue construct.

The anchors preferably include silk suture segments coated with cell adhesion molecules, such as laminin, and the anchors can also include a bone-like substrate. The method of the present invention further includes coating the substrate with cell adhesion molecules, such as laminin or thrombin. For laminin, the preferred concentration is about 1.5 to 3.0 $\mu g/cm^2$. The method preferably further includes incubating the substrate and anchors with a growth medium prior to providing fibroblast cells on the substrate.

Still further, the method according to the present invention includes disposing the fibroblast cells in a growth medium prior to becoming confluent, and disposing the fibroblast cells in a differentiation medium after becoming confluent. Preferably, the method also includes supplementing the fibroblast cells with ascorbic acid, most preferably approximately 100 $\mu g/ml$ of L-ascorbic acid 2-phosphate. The method can further include measuring a functional property of the connective tissue construct, such as tensile strength, and using the measured property as feedback to control the formation of the connective tissue construct.

In further accordance with the present invention, a method is provided for forming a tendon construct, including providing a substrate and securing at least two anchors to the substrate in spaced relationship. The method further includes providing a medium including fibroblast cells and ascorbic acid on the substrate, where at least some of the cells are in contact with the anchors. Still further, the method includes culturing the fibroblast cells in vitro under conditions to allow the cells to self-organize and become confluent between the anchors, where the anchors are receptive to the cells and allow the cells to attach thereto while permitting the cells to detach from the substrate and form a three-dimensional tendon construct.

The above objects and other objects, features, and advantages of the present invention are readily apparent from the following detailed description of the best mode for carrying out the invention when taken in connection with the accompanying drawings.

DETAILED DESCRIPTION OF THE PREFERRED EMBODIMENT(S)

Figure 1:
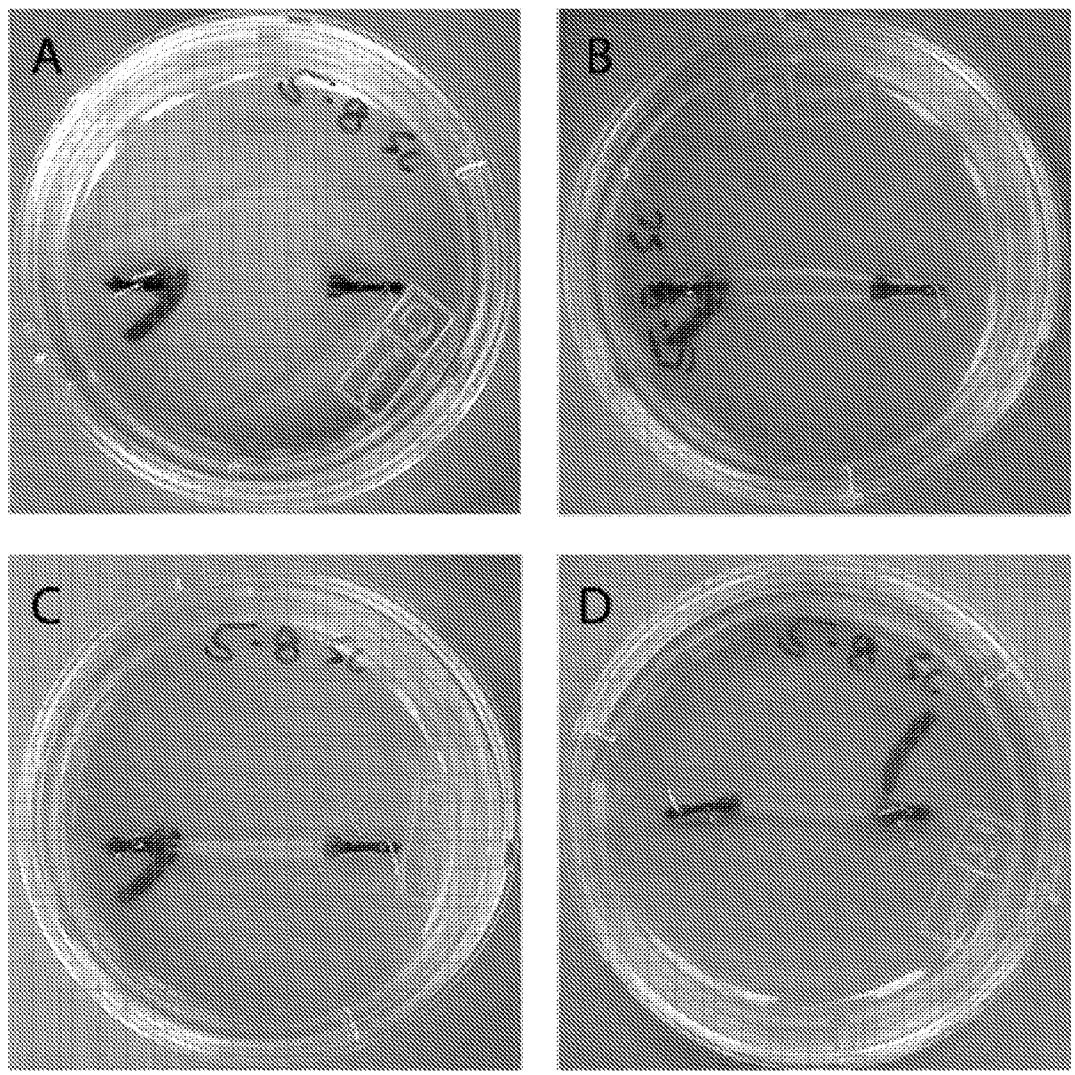
FIGS. 1A-1D show a tendon construct according to the present invention in the process of forming, wherein the construct is shown at (A) 9 days, (B) 12 days, (C) 15 days, and (D) 3 months after plating of fibroblast cells.

The present invention provides a three-dimensional connective tissue construct and a system and method for producing the construct from primary cell culture. A method for the culture of primary skeletal muscle myogenic precursor cells is disclosed in commonly assigned U.S. Pat. No. 6,207,451 which is incorporated by reference herein. According to the present invention, this method has been modified to promote the self-organization of fibroblast cells in vitro to form connective tissue, in particular tendon tissue.

As described herein, precursor cells are defined as any cell which can be used to develop a particular tissue of interest. In the case of tendons, precursor cells include, but are not limited to, fibroblasts. In addition, stem cells, such as bone marrow cells, can be induced to differentiate into tendon precursors as is known in the art.

By way of example, the connective tissue construct and method for producing the construct of the present invention are described with reference to the use of tendon tissue originating from rats. However, the construct and method of the present invention are not intended to be limited to one particular cell origin or age, construct shape, time frame, component concentration, or culture condition. For example, it is fully contemplated that tendon tissue from any mammal, including human beings, could be similarly utilized according to the method described herein. Furthermore, it is contemplated that fibroblast cells could be obtained from body tissues other than tendon, such as ligaments, lung tissue, skin, corneal tissue, or others. One skilled in the art can readily appreciate that various modifications can be made to the method described herein without departing from the scope of the invention disclosed.

As is apparent to those skilled in the art, the culture of cells as described below must be carried out in accordance with commonly practiced cell culture techniques. For example, all materials and media which will be placed in contact with living cells must be appropriately sterilized and handled. In addition, the cells and tendon constructs must be maintained in an otherwise aseptic environment. Of course, it is understood that all reagent measurements and submersion times described herein are approximate, and can be varied slightly without affecting the resulting method.

In the description and data that follow, primary rat tendon fibroblasts were obtained from Achilles tendons harvested from Fischer 344 retired breeder rats (Charles River Laboratories, MA). According to the method of the present invention, Achilles tendon cells are dissociated by placement in a 0.25% trypsin-EDTA solution containing 200 units/ml type I collagenase. The solution is placed in a reciprocal shaking bath at 37° C. for approximately 6 hours to facilitate breakdown of the ECM. After the tissue is dissociated, the cells are pelleted by centrifugation at 100 g for approximately 15 minutes and the supernatant is then removed by aspiration. The cells are resuspended with growth medium (400 ml Ham F-12, 100 ml fetal bovine serum (FBS), 100 units/ml antibiotic-antimycotic) and then expanded in tissue culture flasks. Cells are passaged at ~60% confluence and stored in liquid nitrogen until needed.

An amenable substrate on which to form the tendon constructs is preferably created by coating 35 mm culture dishes with approximately 1.5 ml SYLGARD® (Dow Chemical Corp., Midland, Mich., type 184 silicone elastomer). Of course, another elastomeric polymer having similar non-porous, hydrophobic properties could also be used. After curing for ~2 weeks, the dishes are rinsed with Dulbecco's Phosphate-Buffered Saline (DPBS) or another suitable balanced salt solution, and approximately 2.0 $\mu g/cm^2$ natural mouse laminin is applied as a solution of 9.6 mg/ml laminin in DPBS. The laminin concentration on the substrate is used to control both the rate of cell growth and the time of cell monolayer delamination for the formation of the tendon construct of the present invention. In particular, the laminin disappears from the substrate within a couple of weeks, which facilitates the detachment process to allow tendon construct formation. The optimal value for use in the present invention appear to be in the range of about 1.5 $\mu g/cm^2$ to 3.0 $\mu g/cm^2$. Of course, another cell adhesion protein could also be used in accordance with the present invention. For example, thrombin may also be used to stimulate contractility and therefore facilitate detachment of the cell layer from the substrate. The DPBS is allowed to evaporate overnight in a biological safety cabinet, leaving a layer of laminin-coated SYLGARD®. Dishes are subsequently rinsed with DPBS.

According to a preferred embodiment of the invention, silk suture segments coated with cell adhesion molecules are utilized as anchors, functioning as constraints or guides around which the delaminating cell layer forms the tendon construct. Preferably, the cell adhesion molecules are extracellular matrix (ECM) attachment molecules, most preferably laminin. The anchors are produced by cutting silk suture, preferably size 0, to a convenient length. Lengths of 6 to 8 mm are easily pinned in place, but the length can be varied without limit as dictated by the specific circumstances. The segments of suture are dipped in a solution of 50 µg/ml laminin, preferably natural mouse laminin (Gibco), in DPBS with care taken to thoroughly wet the suture. The suture segments are then allowed to dry before use.

As described in U.S. Pat. No. 6,207,451 incorporated herein by reference, the anchors can alternatively be produced from small acellularized fragments of skeletal muscle, wherein the acellularized fragments have cell adhesion molecules associated therewith. Preferably, the fragments contain ECM attachment molecules, such as laminin, collagen, and pronectin. As still another alternative, a bone-like substrate, synthetic and/or natural (for example, hydroxyapatite or calcium phosphate), could also be used as a possible anchor material, thereby mimicking developmental conditions.

The anchors are preferably pinned approximately 12 mm apart in the prepared culture dish with stainless steel minutien pins. The dishes are then filled with approximately 1 ml growth medium, enough to cover the top of the sutures. The plates are sterilized via ultraviolet irradiation in a biological safety cabinet for approximately 90 minutes, and then placed in an incubator (5% $CO_2$, 37° C.) for 5-8 days prior to seeding with fibroblasts. It is believed that during incubation, the proteins in FBS adhere to the substrate and anchors, thereby enhancing cell adhesion. Although two anchors are used to create the preferred tendon construct shape of the present invention, more anchors may be used to form any desired size or shape of tendon construct.

After incubation, the growth medium is aspirated and preferably approximately $5 \times 10^5$ cells suspended in 2 ml growth medium are seeded onto each culture dish. The plated cells are supplemented with ascorbic acid, preferably approximately 100 µg/ml of L-ascorbic acid 2-phosphate, a stable derivative of ascorbic acid. Ascorbic acid is necessary for the synthesis of collagen, the main constituent of tendons, and promotes the maintenance of a confluent cell layer in this system. Fresh ascorbic acid is added each time the growth medium is changed, every ~2-3 days. When the cells become confluent, after approximately 5 days, differentiation medium (465 ml DMEM, 35 ml FBS, 100 units/ml antibiotic-antimycotic) is substituted for growth medium to induce construct formation. The differentiation medium is changed every ~2-3 days and the culture dishes maintained in an incubator (37° C., 5% $CO_2$) until the constructs are used for testing.

The integrity of the tendon constructs according to the present invention appears to be dependent on the time of media exchange and the ascorbic acid concentration. If the medium is switched to differentiation medium prior to 5 days, viable constructs may not form reliably. This is likely the result of a decrease in the production of ECM and/or the proliferation of the fibroblasts when placed in the low serum differentiation medium, as the concentration of serum has been shown to affect both quantities (see Kang and Kang, *Yonsei Medical Journal*, 40, p. 26, 1999). Furthermore, in the absence of ascorbic acid, a confluent layer of fibroblasts may not be maintained. This is attributed to a decreased ability to form a stable ECM, most importantly type I collagen, which is dependent on the inclusion of ascorbic acid (see Kurata and Hata, *Journal of Biological Chemistry*, 266, P. 9997, 1991).

FIGS. 1A-1D depict the progressive delamination of the two-dimensional cell layer and gradual self-organization into the three-dimensional tendon construct according to the present invention. In accordance with the present invention, the formation of a tendon construct typically begins with peripheral delamination of the edges of tendon tissue from the substrate, as shown in FIGS. 1A and 1B. The delamination process typically commences at 14 to 21 days, corresponding with the disappearance of laminin from the substrate, and progresses radially inward until the entire cell monolayer has peeled away from the substrate material, as shown in FIG. 1C. The constructs are then supported between the anchors above the SYLGARD® substrate under self-mediated tension. When probed with tweezers, the tendon constructs are noticeably taut, and when released from one anchor, the constructs contract slightly. The delaminating monolayer will eventually roll up and lift off of the substrate to form a three-dimensional structure between the two anchors, as shown in FIG. 1D. The self-assembling process of the tendon constructs of the present invention is highly repeatable.

Following the switch from growth to differentiation medium, the tendon constructs form in about two weeks. No external influence is necessary for the cell layer to detach from the sides of the culture dish and SYLGARD®. The tendon constructs of the present invention can be maintained in culture for greater than 15 weeks, wherein the time depends upon such conditions as the density at which the cells are plated, the anchor material and spacing, the frequency of feeding, and the type and density of the substrate cell adhesion molecules, such as laminin. There should be no limitations on the length or diameter of the tendon constructs that can be created.

Figure 2:
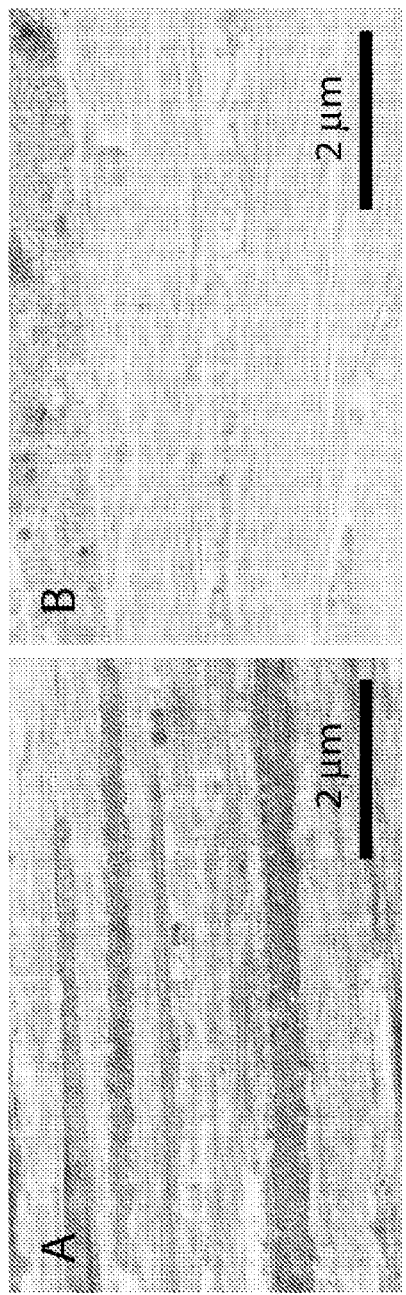
FIGS. 2A and 2B are light micrographs of longitudinal sections of a tendon construct according to the present invention and neonatal tendon, respectively.

For morphological analyses, the resulting tendon constructs of the present invention, along with native neonatal Achilles tendons harvested from 2 day old Fisher 344 pups, were fixed in a 3% formaldehyde/glutaraldehyde in 0.1 M sodium cacodylate buffer solution pH=7.4 (Electron Microscopy Sciences, Fort Washington, Pa.) at 4° C. and embedded in EPON (Ted Pella Inc., Redding, Calif., Eponate 12 resin). For light microscopy, semi-thick sections, 1 μm, were cut with an ultramicrotome, mounted on glass microscope slides, and stained with 1% (w/v) Toluidine Blue solution (FIG. 2). Ultrathin slices, 50 nm, were cut for electron microscopy and were mounted on uncoated copper grids and stained with aqueous uranyl acetate and lead citrate. The ultrastructure of the constructs was investigated using a transmission electron microscope at 60 kV (FIG. 3).

Figure 3:
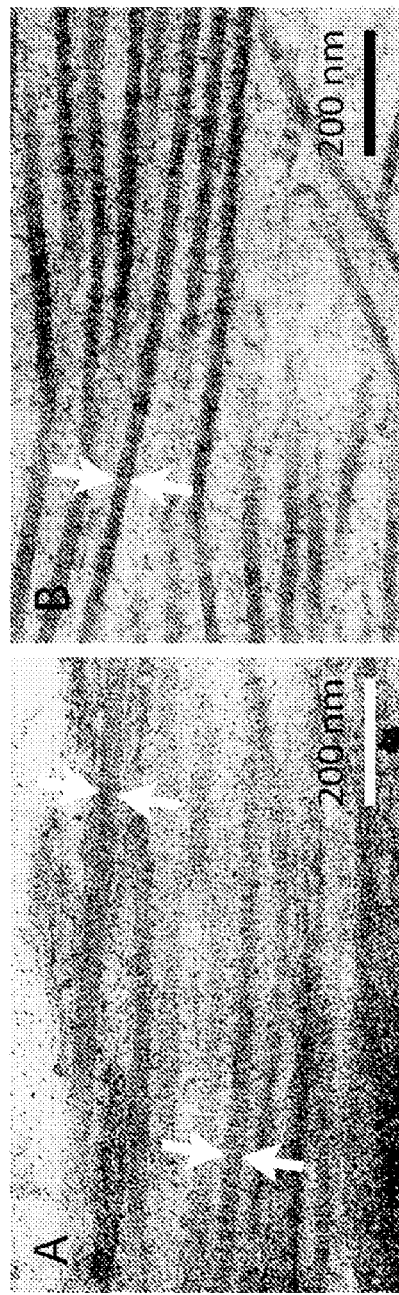
FIGS. 3A and 3B are electron micrographs of longitudinal sections of a tendon construct according to the present invention and neonatal tendon, respectively.

FIGS. 2 and 3 provide a morphological comparison of a representative tendon construct according to the present invention and a neonatal rat tendon. As one skilled in the art will readily appreciate, the longitudinal sections shown in FIGS. 2A and 3A clearly display an ultrastructural morphology similar to that of the neonatal rat Achilles tendon shown in FIGS. 2B and 3B. Comparing FIGS. 2A and 2B, it is noted that both the tendon construct of the present invention and the neonatal tendon are highly cellular, and include some disorganized ECM surrounding the collagen fibrils. At higher magnification (FIGS. 3A and 3B), it is evident that the fibril diameter is similar (~50 nm, as indicated by arrows) in both the tendon construct and the neonatal tendon, wherein the fibrils display the characteristic periodic striations of type I collagen.

For mechanical testing, tendon construct diameter was first measured at several positions along the length using an inverted microscope, and an average diameter was calculated using all measured values. Tensile testing was performed using an 810 Material Testing System (MTS Systems Corp., Eden Prairie, Minn.) outfitted with a custom optical 200 mN load cell (see Dennis and Kosnik, *In Vitro Cellular Developmental Biology—Animal*, 36, p. 327, 2000) and grips machined from DELRIN® (Acetal). The grips clamped the specimens via an adjustable set screw. Data acquisition and control were performed using LabVIEW software (National Instruments, Austin, Tex.) on a computer. The load cell was zeroed before the attachment of each sample. Samples were moistened by regularly applying drops of DPBS with a Pasteur pipette, as drying out of specimens has been shown to significantly alter the mechanical properties of tendons and other soft tissues. The gauge length was taken to be the length of the construct between the grips which was measured with digital calipers after inserting and clamping the sample into both grips and applying a prestress of approximately 4 kPa. The force associated with this prestress, 1 mN, was 0.4% of the full range of the load cell, and roughly twice its resolution limit. The samples were tested at a constant true strain rate of $0.05\ s^{-1}$.

Figure 4:
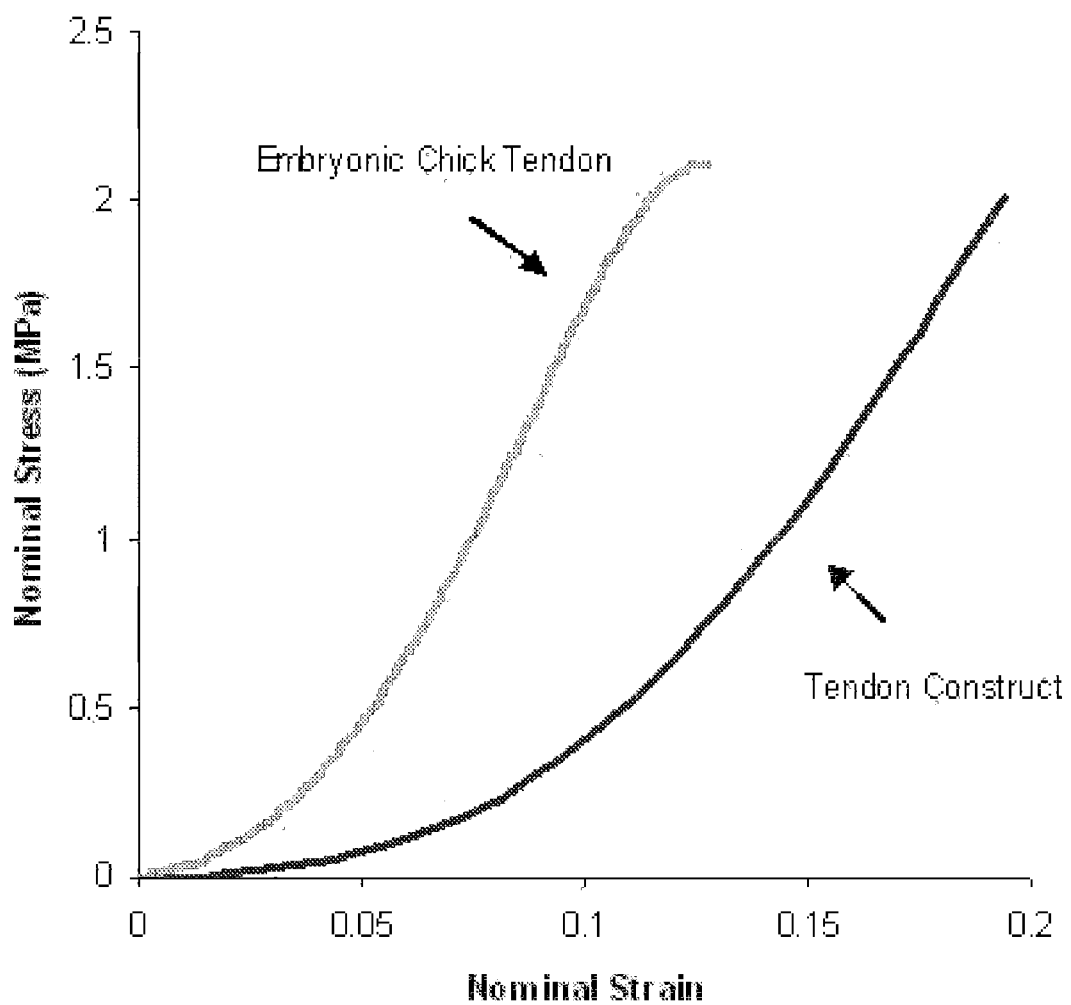
FIG. 4 is a graph of the stress-strain response of tendon constructs according to the present invention compared with the stress-strain response of embryonic tendon.

As depicted in FIG. 4, the stress-strain response of the tendon constructs of the present invention closely resembles that of immature tendon. The initial response is compliant and resembles the well-known toe region of soft tissue response. At a nominal strain of 0.05, the tangent modulus, or the slope of the tangent to the stress-strain curve, markedly increases, and the stress-strain response is approximately linear in the strain range of 0.11 to 0.19 at which point the construct failed by breaking in one of the grips. The tangent modulus measured at a strain of 0.16, within the linear region of the response, is 20 MPa. The tendon constructs of the present invention are thus mechanically similar to embryonic chicken extensor tendons which have a tangent modulus of 27 MPa (see McBride et al., *International Journal of Biological Macromolecules*, 10, p. 194, 1988). In fact, the ultimate tensile strength of the tendon constructs may be larger than reported here since the majority of the constructs failed at either the upper or lower grip. This is attributed to the pressure applied by the grip due to manual tightening that could result in localized lateral compression of the construct at that interface, and the introduction of a stress concentrator.

Therefore, the tendon constructs according to the present invention not only display the non-linear response characteristic of soft tissues, but they have similar mechanical parameters to embryonic tendon. The ultimate tensile strength and tangent modulus of the tendon constructs and embryonic chick tendon are very similar (FIG. 4). One difference between the tissues is the strain at failure, 0.12 for chick tendon and 0.19 for the constructs, but this may be attributed to the testing procedure rather than the intrinsic material properties of the tissues. It is unknown whether or not McBride et al. preloaded their specimens which would decrease the length of the toe region, and consequentially the strain at failure. Another cause of this discrepancy may result from the drying out of the specimens. While both procedures entailed the periodic wetting of the tissues, the degree of hydration may have been different in each of the tissues. As tendons dry out, the stiffness increases and the toe region becomes shorter.

The present invention demonstrates the ability to induce primary tendon fibroblasts to secrete and organize their own ECM, and under the right conditions to self-assemble into three-dimensional constructs without the aid of exogenous scaffolding. The resulting tendon constructs are both structurally and functionally similar to embryonic tendons. The ECM gives the construct mechanical properties close to that of the replaced tendon so that mobilization can resume as soon as possible, accelerating the process of healing.

The findings herein suggest that under the right conditions, tendon fibroblasts rebuild tendon morphology by recapitulating the embryonic state. This return to a primitive state has also been shown in studies of tendon repair and may provide a mechanism to increase tendon plasticity (see Postacchini and Demartino, *Connective Tissue Research,* 8, p. 41, 1980). The work of Postacchini and Demartino on the repair of tendon after partial tenotomy demonstrated that, during repair, tendon morphology progresses from developmental to mature in ~16 weeks. The first collagen fibrils produced have small diameters, 20-80 nm. The fibrils continue to mature, and after sixteen weeks the fibrils possess a diameter of 200-300 nm. The regenerative pattern of tendon in vivo admits the hypothesis that the tendon constructs of the present invention have the capacity to mature in vitro when incubated in the proper environment. Interestingly, fibroblasts would not necessarily have been expected to self-organize in the same manner that a culture of myotubes would self-organize, principally because fibroblasts do not generate the same magnitude of forces in vitro as myotubes.

A tendon construct as described herein could be engineered, transected, and the two halves used as artificial tendon anchors for the formation of a muscle construct formed as described in U.S. Pat. No. 6,207,451. Alternatively, a tendon construct and a muscle construct can each be severed and placed in close proximity to one another to form a myotendinous junction. Cross-links can be removed locally at the severed ends of the constructs, for example by using microfluidics or solutions containing reducing agents. The end of the tendon construct can then be seeded with myoblasts and the end of the muscle construct seeded with fibroblasts along a controlled gradient. Still further, a co-culture of fibroblasts and myoblasts could be created, for example, by temporal plating of cells, spatial plating cells, or adhesion protein patterning on the substrate.

The connective tissue constructs according to the present invention have a variety of foreseeable applications, ranging from transplantation in vivo to functional and pharmacological testing in vitro. These constructs are potentially useful for studying the developmental biology of tendon as well as for clinical use in tendon repair and screening for disease. The functional capability of the tendon constructs shown in FIG. 4 demonstrates their ability to be used as an in vitro model of tendon tissue, allowing the comparison of functional data from the tendon constructs with the pool of published data for tendon tissue in the scientific and clinical literature. Furthermore, the constructs could be used in the engineering of tissue-to-tissue or tissue-to-machine interfaces to provide the necessary mechanical impedance matching and functional interface to allow efficient and biologically appropriate integration.

With reference to commonly assigned U.S. Pat. Nos. 6,114,164 and 6,303,286, both incorporated by reference herein, the formation of the connective tissue constructs of the present invention can be guided by measuring a functional property of the construct and subsequently using the measured property as feedback. For example, the tensile strength of the tendon constructs could be determined prior to failure, and this functional measure could then be used in a feedback control loop to guide the tendon construct to a desired phenotypic outcome.

The connective tissue constructs also have the potential to be used in studies of ligament function and replacement. Tendons and ligaments are generally grouped together in the literature since these tissues possess similar structural and mechanical characteristics, but there are also subtle differences that have not been thoroughly investigated. There is generally a larger and more variable amount of elastin in ligaments, and the development and biochemical content of tendons and ligaments have been shown to differ. These differences may be the result of phenotypically different fibroblasts, loading environment, or extrinsic signals. The formation of analogous constructs using ligament fibroblasts may help to identify the phenotypic and mechanical differences between these tissues. As described herein, the constructs have been defined as tendon-like structures since the fibroblasts used are derived from tendons. However, it is understood that the method of the present invention can be utilized to produce other connective tissue constructs, such as a ligament construct, in addition to the tendon construct shown and described herein.

The tendon constructs described herein have the potential to aid in further elucidating the factors that influence tendon development. Using the tendon constructs, the role of specific growth factors, genes, or mechanical forces in tendon development can be studied in isolation, eliminating the confounding variables present in vivo. For example, it is generally accepted that mechanical interventions influence tendon development, but there have been few studies that explicitly address this issue. The greatest difficulty in determining the role of force on tendon development has been the isolation of the effect that force has on the tissue, independent of the influence of concurrent alterations to adjacent tissues and the overall hormonal environment. The tendon constructs of the present invention may provide the necessary isolated environment needed to decipher the role these factors play.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for forming a connective tissue construct, comprising:
   providing a substrate;
   securing at least two anchors to the substrate in spaced relationship;
   providing fibroblast cells in a growth medium on the substrate without disposing the cells within an exogenous scaffold material, wherein at least some of the cells are in contact with the anchors and attach thereto such that the fibroblast cells grow to confluency; and
   replacing the growth medium with a differentiation medium to induce construct formation, the differentiation medium having a lower serum concentration than the growth medium, such that the fibroblast cells detach from the substrate and form a three-dimensional connective tissue construct.

2. The method according to claim 1, wherein providing fibroblast cells includes deriving the fibroblast cells from tendon tissue.

3. The method according to claim 1, wherein providing the fibroblast cells includes deriving the fibroblast cells from stem cells.

4. The method according to claim 1, wherein culturing the fibroblast cells allows the cells to self-organize to form the three-dimensional connective tissue construct.

5. The method according to claim 1, wherein the anchors include silk suture segments coated with cell adhesion molecules.

6. The method according to claim 5, wherein the cell adhesion molecules include laminin.

7. The method according to claim 1, wherein the anchors include at least one of hydroxyapatite and calcium phosphate.

8. The method according to claim 1, further comprising coating the substrate with cell adhesion molecules.

9. The method according to claim 8, wherein the cell adhesion molecules include laminin.

10. The method according to claim 9, wherein the concentration of laminin is about 1.5 to 3.0 µg/cm².

11. The method according to claim 8, wherein the cell adhesion molecules include thrombin.

12. The method according to claim 1, further comprising incubating the substrate and anchors with a growth medium prior to providing fibroblast cells on the substrate.

13. The method according to claim 1, further comprising supplementing the fibroblast cells with ascorbic acid.

14. The method according to claim 13, wherein the ascorbic acid includes approximately 100 µg/ml of L-ascorbic acid 2-phosphate.

15. The method according to claim 1, further comprising measuring a functional property of the connective tissue construct and using the measured property as feedback to control the formation of the connective tissue construct.

16. The method according to claim 15, wherein the functional property includes a tensile strength of the connective tissue construct.

17. The method according to claim 1, further comprising culturing myogenic precursor cells in combination with the fibroblast cells.

18. The method according to claim 1, further comprising harvesting the fibroblast cells from mammalian tissue.

19. The method according to claim 1, further including implanting the connective tissue construct in a suitable recipient.

20. A method for forming a tendon construct, comprising:
providing a substrate;
securing at least two anchors to the substrate in spaced relationship;
providing a growth medium including fibroblast cells and ascorbic acid on the substrate without disposing the cells within an exogenous scaffold material, wherein at least some of the cells are in contact with the anchors and attach thereto such that the fibroblast cells grow to confluency; and
replacing the growth medium with a differentiation medium to induce construct formation, the differentiation medium having a lower serum concentration than the growth medium, such that the fibroblast cells detach from the substrate and form a three-dimensional tendon construct.

21. The method according to claim 20, wherein culturing the fibroblast cells allows the cells to self-organize to form the three-dimensional tendon construct.

22. The method according to claim 20, wherein the anchors include silk suture segments coated with cell adhesion molecules.

23. The method according to claim 22, wherein the cell adhesion molecules include laminin.

24. The method according to claim 20, wherein the anchors include at least one of hydroxyapatite and calcium phosphate.

25. The method according to claim 20, further comprising coating the substrate with cell adhesion molecules.

26. The method according to claim 25, wherein the cell adhesion molecules include laminin.

27. The method according to claim 26, wherein the concentration of laminin is about 1.5 to 3.0 µg/cm².

28. The method according to claim 25, wherein the cell adhesion molecules include thrombin.

29. The method according to claim 20, further comprising incubating the substrate and anchors with a growth medium prior to providing fibroblast cells on the substrate.

30. The method according to claim 20, wherein the ascorbic acid includes approximately 100 µg/ml of L-ascorbic acid 2-phosphate.

31. The method according to claim 20, further comprising measuring a functional property of the connective tissue construct and using the measured property as feedback to control the formation of the tendon construct.

32. The method according to claim 31, wherein the functional property includes a tensile strength of the tendon construct.

33. The method according to claim 20, further comprising culturing myogenic precursor cells in combination with the fibroblast cells.

34. The method according to claim 20, further comprising harvesting the fibroblast cells from mammalian tissue.

35. The method according to claim 20, further including implanting the tendon construct in a suitable recipient.

36. The method according to claim 20, wherein replacing the growth medium with the differentiation medium occurs after about 5 days.

37. The method according to claim 1, wherein replacing the growth medium with the differentiation medium occurs after about 5 days.

* * * * *